United States Patent [19]

Corbic

[11] 4,165,594
[45] Aug. 28, 1979

[54] PACKAGING OF A PRODUCT IN A STERILE MEDIUM

[75] Inventor: Yves J. Corbic, Chatou, France

[73] Assignee: Société dite: Gatrun Anstalt, Vaduz, Liechtenstein

[21] Appl. No.: 903,963

[22] Filed: May 8, 1978

[30] Foreign Application Priority Data

May 10, 1977 [FR] France .................. 77 14286
May 16, 1977 [FR] France .................. 77 14954

[51] Int. Cl.² ............................................. B65B 55/04
[52] U.S. Cl. ....................................... 53/453; 53/167;
53/425; 53/559
[58] Field of Search ............... 53/425, 426, 453, 167, 53/559

[56] References Cited

U.S. PATENT DOCUMENTS 3,911,640 10/1975 Rausing .................. 53/426
3,942,299 3/1976 Bory .................... 53/453 X Primary Examiner—Travis S. McGehee
Attorney, Agent, or Firm—Bacon & Thomas

[57] ABSTRACT

A joint strip is used comprising a container strip in thermoplastic material and a cover strip having sterile sides facing one another and isolated from the outside in a sealed manner along their edges. The container and cover strips are separated each from the other at the entrance to a sterile enclosure, the cover strip passing along a path which overhangs that of the container strip and passes above stations for forming containers in the container strip, and for filling the containers. The cover strip is exposed, on the side of its sterile face, to a sterile atmosphere whose pressure is slightly in excess of that of the outside. The cover and container strips are moved respectively above and below a non-sterile area containing elements of the forming and filling stations. After the containers carried by the container strip have been filled, the cover and container strips are again joined in a sealed manner along their edges outside the sterile enclosure.

16 Claims, 15 Drawing Figures

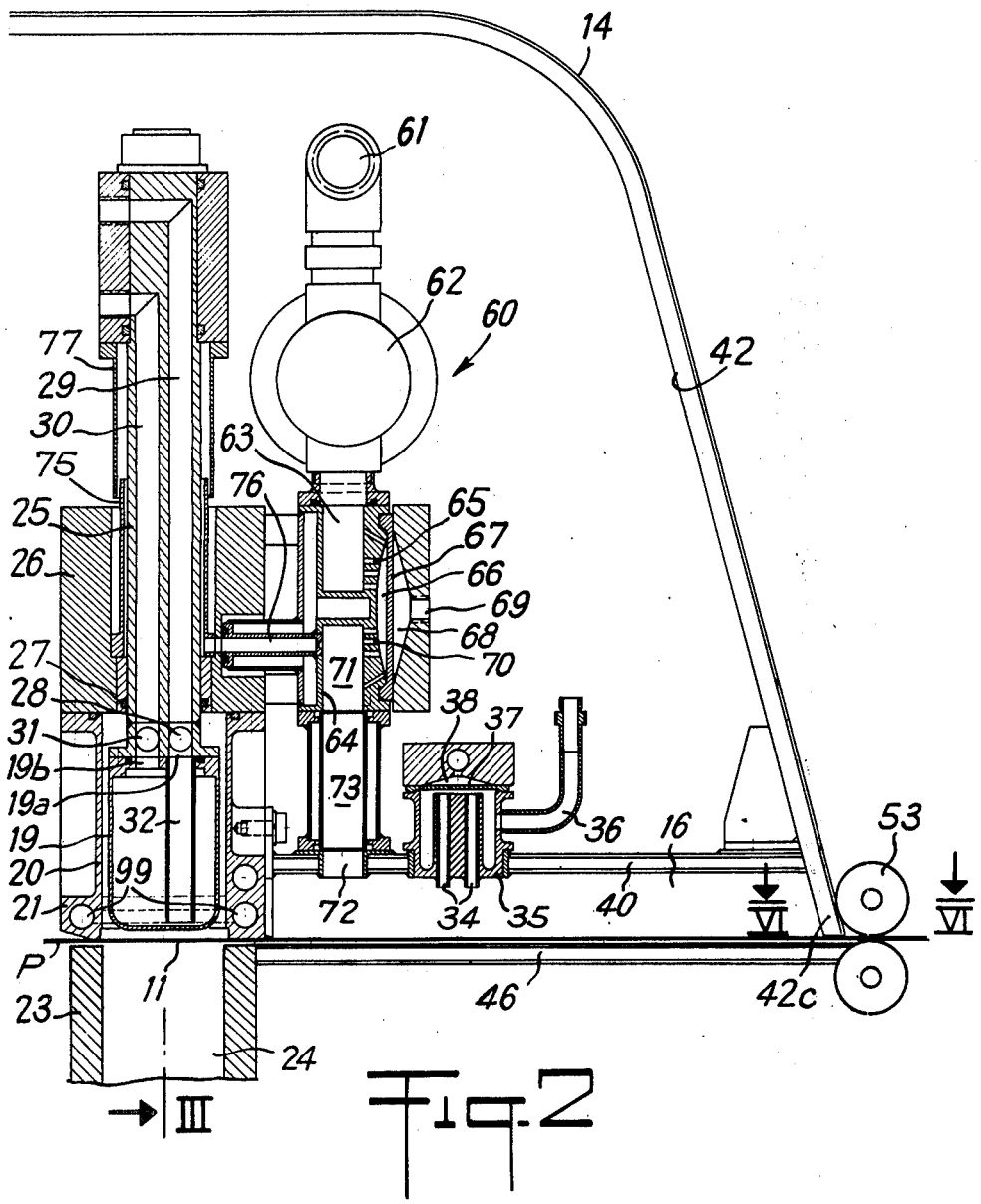

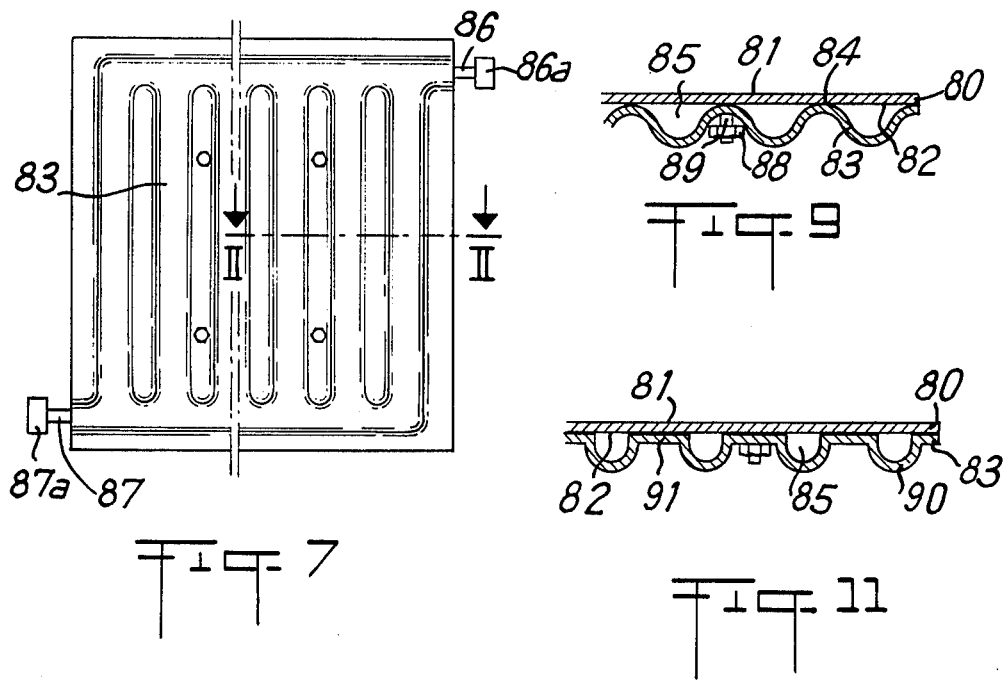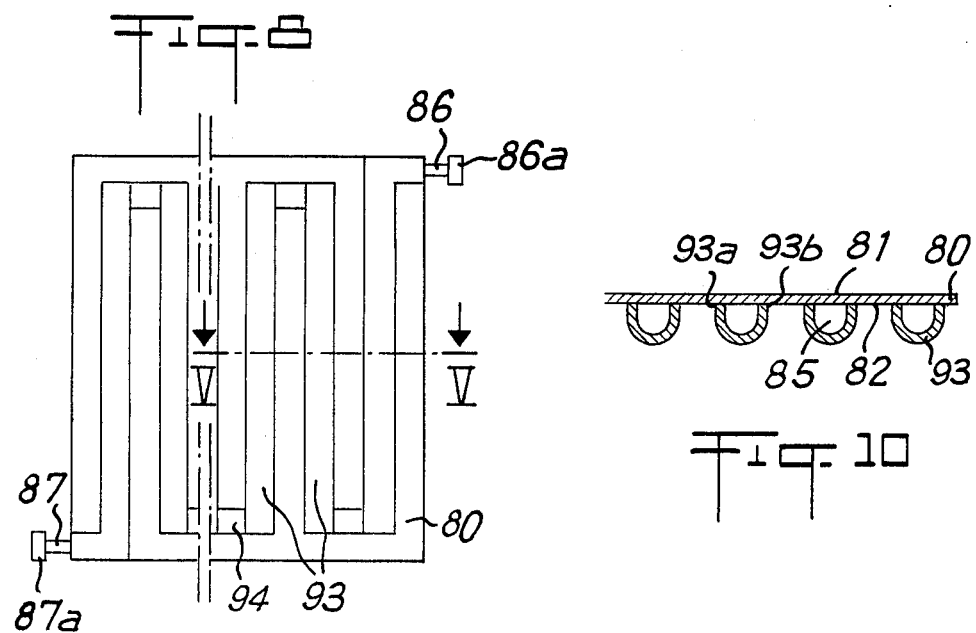

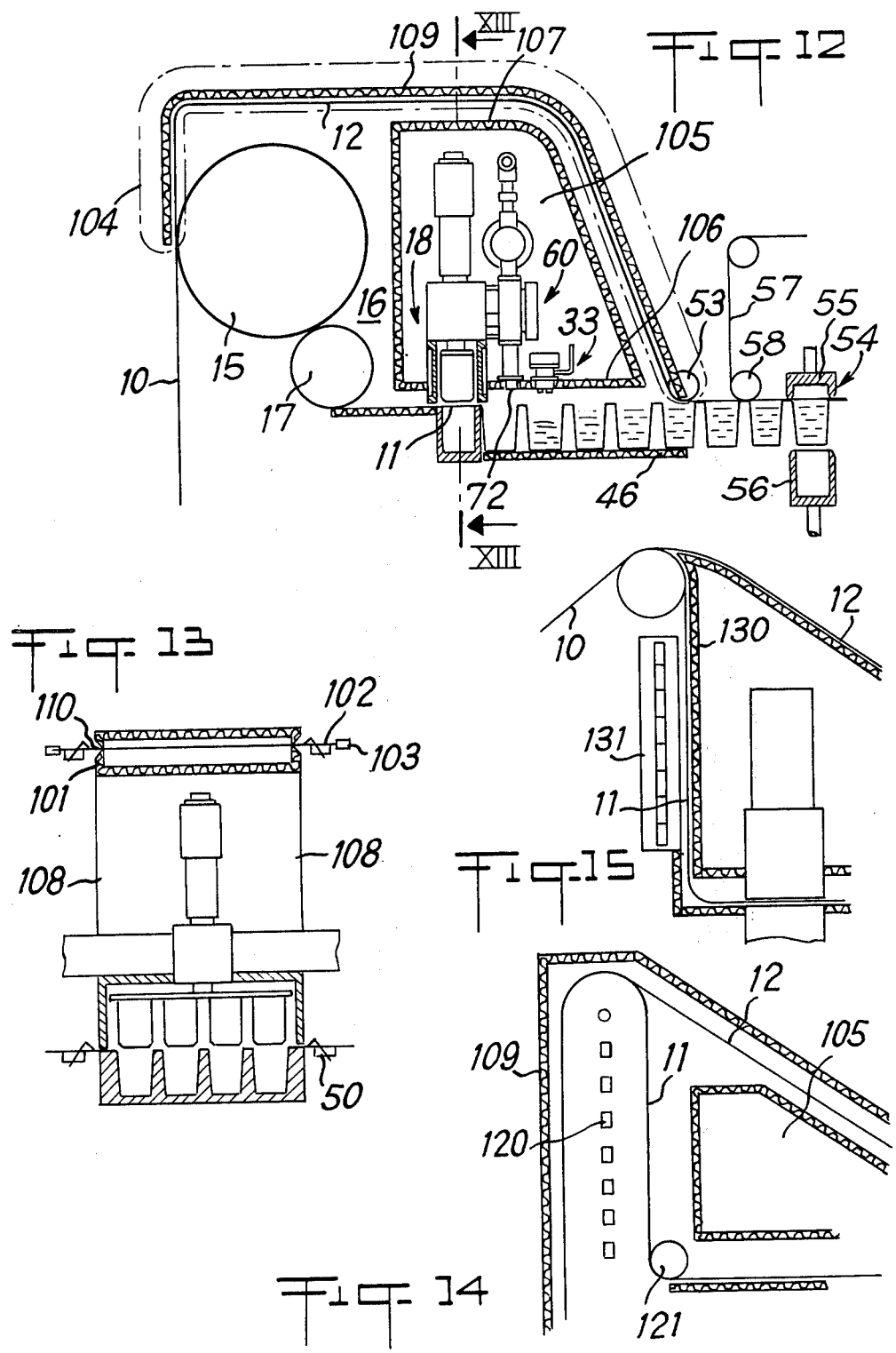

PACKAGING OF A PRODUCT IN A STERILE MEDIUM

The present invention relates to a process for packing a product in a sterile medium wherein containers are formed in a strip of thermoplastic material by hot forming of the thermplastic material in a forming station, the container strip being sterile at least on the side forming the inside of the containers, the formed containers being filled in a filling station, the forming and filling of the containers being made in a sterile enclosure in which a slight excess pressure prevails as compared with the non-sterile external atmosphere, and which enclosure comprises side walls and an upper wall, as well as a bottom wall constituted, at least in part, by the container strip, the filled containers being covered with a strip without their inside being able to become contaminated by the non-sterile atmosphere, at least the face of said strip facing the inside of the containers being sterile, and the cover strip being sealed on the container strip around the filling opening of each container.

The present invention is applicable to the packing of perishable foodstuffs, particularly milk products, or pharmaceutical products.

The chief difficulties of the known processes of the above-indicated type consist in the performing in the most economical possible way of the sterilisation of the enclosure when a packing operation starts, and of the feed of container strips and cover strips with at least one sterile side for each.

If heat sterilisation of a cover strip does not pose too many problems, to the extent to which said strip is able to withstand a fairly high temperature, it is not so with the thermoplastic container strip. Indeed, it is often indicated that the sterilization of the thermoplastic strip is performed by the heat supplied to said strip to bring it to the forming temperature. For a satisfactory sterilisation, it is necessary to heat the strip to a certain temperature for a certain period of time, the minimum sterilisation time being all the shorter as the sterilisation temperature is the higher. But, the conditions of a good sterilization may be attained by heating the strip simply to forming temperature only if the time during which the strip is held at that temperature is relatively long. For a machine of the known type for the packing of milk products in heat-formed containers this demands, if it is desired to retain an adequate production rate in terms of economic profitability, requiring the thermoplastic strip to travel over several meters in a heating tunnel. The result would be much too considerable an overall size, obvious danger of overheating the strip in the event of an even temporary stop of the strip, and lengthy starting with the danger of a substantial loss of material.

For the initial sterilisation of the enclosure it is known to use a sterilizing product, which is applied on the internal sides of the walls, or even with which the enclosure is filled, then a sterile atmosphere is created with slight excess pressure. This modus operandi requires using a sterilizing product, which is generally reluctantly accepted in the case of the packing of foodstuffs. Moreover, it is necessary to proceed most carefully, which therefore requires time, particularly when the enclosure contains several chambers and has walls with cavities, corners, and other areas of difficult access.

The invention has for its object to provide a sterile packing process permitting the best possible solution of the problems of sterilization of the walls of the sterile enclosure and effecting the feed under very good conditions of container strips and cover strips having a perfectly sterile side.

This aim is achieved by a process according to which, in accordance with the invention, use is made of a composite strip constituted by at least the container strip and the cover strip having each a sterile side isolated from outside by application on another sterile side, in seal-tight manner, at least along its sides, the sterile sides of the container strips and cover strips being made to face each other, the container strip and the cover strip are separated at the entrance to the sterile enclosure, the cover strip is made to travel along a path overhanging that of the container strip, and it passes above forming and filling stations, a sterile atmosphere is made to prevail with slight excess pressure relatively to the non-sterile outside atmosphere on the side of the sterile face, turned downwards, of the cover strip, the container and cover strips are moved along walls provided with incorporated heating means by causing them to pass respectively below and above a non-sterile area containing elements of forming and filling stations, and, outside the sterile enclosure, the cover strip and the container strip carrying the filled containers are joined together in seal-tight manner at least along their edges.

The introduction of the container strip alone into the sterile enclosure, by the separation of a strip which covered its sterile side in seal-tight manner, permits the separation of the operations of sterilization of the container strip and of heating said strip to make it reach forming temperature. In particular, it will be possible to use a prefabricated composite strip and, according to a peculiarity of the process in accordance with the invention, the container strip is heated to bring it to forming temperature along its path situated between the entrance to the sterile enclosure and the entrance to the forming station, a path where, preferably, it constitutes already at least a part of wall of the sterile enclosure.

In the same way as the operator has a container strip with a sterile side at the entrance to the sterile enclosure, he has a cover strip with a sterile side, a cover strip which is made to pass above a non-sterile area containing elements of forming and filling stations. Thus, it is possible to house a maximum number of elements of said stations outside the sterile enclosure. As, moreover, the joining of the container and cover strips effected in seal-tight manner at least along their sides is carried out outside the sterile enclosure, the sterilization and keeping in the sterile state of said enclosure and considerably simplified.

The travel of the container and cover strips alongside walls provided with incorporated heating means, when starting a packing operation, permits performing the sterilization of the end sections of container and cover strips. Indeed, the enclosure being formed when the end sections of the container and cover strips are joined at the delivery end of the enclosure, there is a contamination of the previously sterile sides of said strip sections, and it is necessary to sterilize said sides at the same time as the internal surfaces of the other walls of the enclosure and as the creation of a sterile atmosphere. The sterilization of the inner sides of said strip sections is effected by the heat radiated as a consequence of the heating of the walls along which these sections are found.

Keeping a sterile atmosphere with a slight excess pressure on the side sterile side of the cover strip permits avoiding a contamination of said side.

According to a particular method of embodiment of the process according to the invention, the cover strip, along its clean path, between the entrance to, and the exit from the sterile enclosure, is made to pass through a channel in the form of a slide or chute whose bottom wall faces the sterile side of the cover strip and is provided with incorporated heating means and whose side walls cover the strip at least along its marginal areas, and there is created, in the space comprised between the bottom of the channel and the sterile side of the cover strip, a sterile atmosphere with a slight excess pressure in relation to the non-sterile external atmosphere.

According to an alternative embodiment of the process, the cover strip is used to form at least partly the upper wall of the sterile enclosure and the cover strip and the container strip, between the entrance to, and the exit from the sterile enclosure, are made to pass respectively above and below a non-sterile transversal tunnel which goes through the sterile enclosure, is isolated from it in seal-tight manner, opens outside and contains upper elements of the forming and filling stations.

Other peculiarities and advantages of the process according to the invention will become clear on reading the description given hereinafter, as an indication but not limitatively, with reference to the attached drawing in which:

FIG. 2 is a view on an enlarged scale of the forming and filling stations of an installation of the type of that represented in FIG. 1;

FIGS. 7 and 8 are elevations of parts of enclosure walls according to the invention;

FIGS. 9 and 10 are cross-sectional views along lines IX—IX and X—X of FIGS. 7 and 8;

FIG. 11 is a cross-sectional view of an alternative embodiment of a part of wall according to the invention;

FIG. 12 is a very diagrammatic view in elevation and cross-section illustrating another method of embodiment of the installation according to the invention;

FIG. 13 is a half view on a very enlarged scale and in cross-section along line XIII—XIII of FIG. 12; and FIGS. 14 and 15 are two very diagrammatic partial views in elevation and in cross-section illustrating alternative embodiments of the installation represented in FIG. 12.

Figure 1:
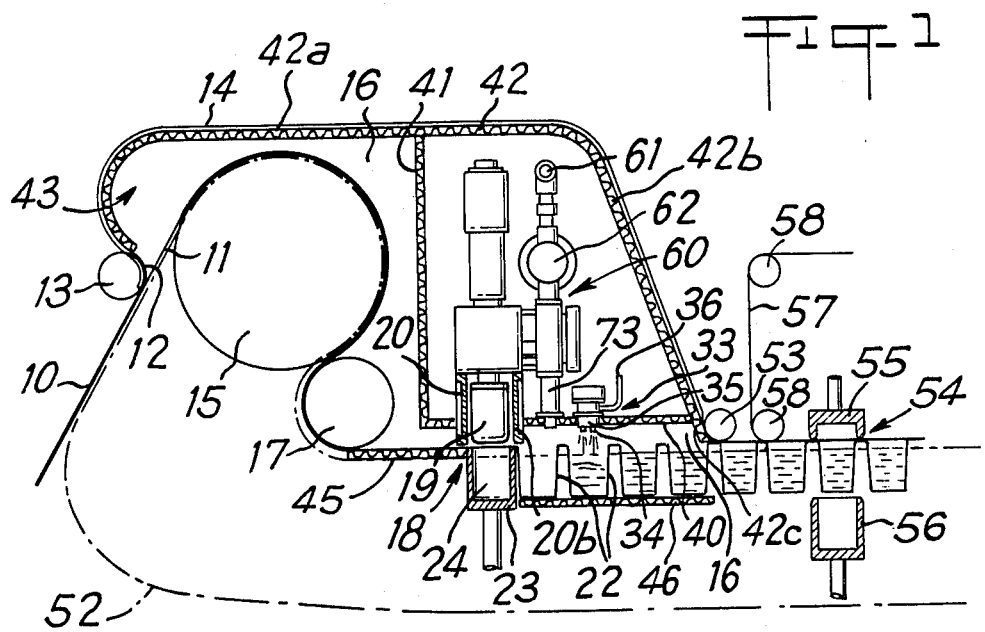
FIG. 1 is a very diagrammatic elevation and cross-sectional view of an installation according to the invention.

The installation, represented very diagrammatically, in FIG. 1, receives a joint strip comprising a strip 11, known as "container strip", and a strip 12, known as "cover strip", applied one against the other in seal-tight manner at least along their sides. The side of the container strip 11 intended to constitute subsequently the inside of the containers and the side of the cover strip 12 facing the inside of the containers are situated facing each other and are sterile.

Strips 11 and 12 are able to be separated from each other under the action of low tensile forces, a separation which may possibly be facilitated by heating the joint strip to a temperature known as separation temperature slightly greater than ambient temperature, but substantially less than the forming temperature to which strip 11 is subsequently heated.

The strip 11 is in thermoplastic material and the cover strip 12 may, for example, be of cellulose material such as paper or cardboard or of metal, such as aluminium or a metal alloy, or even a plastic material.

The joint strip 10 may be made in a sterile medium by heating, and keeping, the material constituting the strips 11 and 12, to sterilization temperature for a period sufficient for their sterilization, then joing them together, again in a sterile medium, by heat sealing or sealing and in tight manner, at least on their border areas.

The joint strip 10 may also be produced by extruding the thermoplastic material of the container strip on the cover strip 12 heated to sterilization temperature, or by co-extruding the individual strips forming the joint strip, the sterilization of the sides facing these individual strips resulting from their manufacture without requiring subsequent treatment.

The cover strip 12 is separated from the container strip 11 as it passes over a cylinder 13. The cover strip 12 is guided along a channel in the form of a slide 14, while the container strip is fed to a heating drum 15. The line of separation between the strips 11 and 12 defines the entrance to a sterile enclosure 16.

The container strip 11 passes over the heating drum 15, being in contact with a relatively substantial part of the periphery of the latter, and over a heating cylinder 17 which returns it along a horizontal plane P which constitutes the plane of transport of the strip 11 through the remainder of the installation. Drum 15 and cylinder 17 are heated, for example, by the circulation of a hot fluid in internal passages formed in the vicinity of their peripheral area, and are situated preferably above the horizontal plane containing plane P.

When it leaves cylinder 17, the strip 11 is at forming temperature and reaches a forming station 18.

Figure 3:
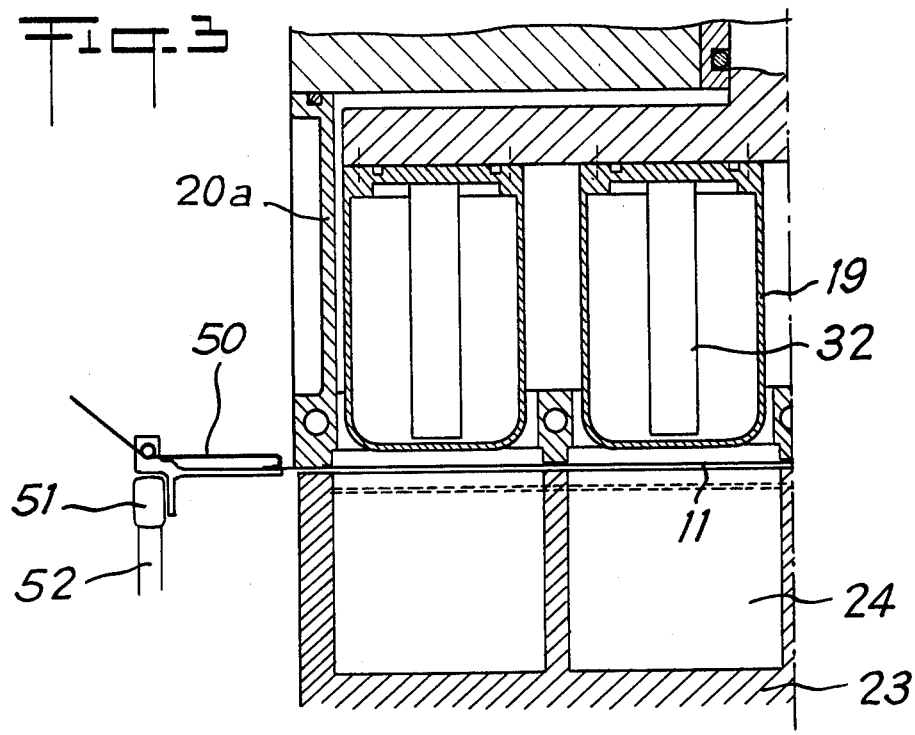
FIG. 3 is a partial half view, on a further enlarged scale, in cross-section along line III—III of FIG. 2.

Said station (FIGS. 1, 2 and 3) comprises at least one and generally several forming punches 19 which are mobile vertically under a forming bell 20 whose bottom edge 21 is situated immediately above Plane P. For the forming of containers 22 in the strip 11 (FIG. 1), the punches 19 cooperate with a mould 23 having several cells 24 whose number correspond to that of punches 19 and whose shape to that of the containers.

The mould 23 is mobile vertically between an upper moulding position (FIGS. 1 to 3) for which its upper edge applies the strip 11 against the bottom edge 21 of the forming bell 20, and a bottom position for which the mould 23 frees the path for the containers formed by hot forming of the thermoplastic material in the cells 24 and borne by the remainder of the strip situated in Plane P.

The punches 19 are fixed on the bottom end of a rod 25 mobile vertically to be able to push the thermoplastic material into the cells 24 during moulding. The rod 25 is guided vertically in a sleeve 26 (FIG. 2) which forms the top of the forming bell 20, with the interposition of at least one sealing ring 27.

The punches 19 are hollow and are thermostated by fluid circulation. A feed circuit 28 connected to an internal longitudinal duct 29 of the rod 25 supplies in parallel the internal volumes of the punches 19 through openings 19a formed in the upper wall of the latter. Moreover, the internal volumes of the punches 19 are connected, through openings 19b adjacent to openings 19a, in parallel onto an outflow duct 30 connected to a longitudinal internal duct 31 of the rod 25. The passages 29 and 30 may be connected respectively to the recycling output and input of a fluid feeding circuit in such a manner as to adjust the temperature of the punches 19 by fluid circulation inside them. To ensure the uniform circulation of the fluid against the whole of the walls which delimit the internal volumes of the punches 19, tubes 32 extend from the openings 19a to near the bottom of the inner space of the punches 19. Thus, the fluid supplied along the channel 29, the duct 28 and the tubes 32 flows along the bottom and side walls of the punches 19 before coming out through the openings 19b made in the upper walls of these punches.

Downstream of the forming station 19 is the filling station 33. This station comprises filling nozzles 34 in a number at least equal to that of the containers to be filled simultaneously, borne by a nozzle support 35. The product to be packed is brought to the station 33 by a duct 36. Metered amounts of product are dispensed into the containers. A flexible sealing membrane 37 is applied against the openings giving access to the nozzles, by sending a pressurized fluid into a chamber 38 situated on one side of the membrane 37, to interrupt the dispensing of product.

The nozzle support 35 is mounted in seal-tight manner on a horizontal wall 40 which overhangs the transport plane P of the strip 11 and is connected in seal-tight manner to the wall of the forming bell 20. The horizontal wall 40 forms, with the strip 11 bearing the filled containers, the upper and bottom walls of the forward part of the sterile enclosure 16. Preferably, the wall 40 is situated at as short as possible a distance from plane P, in particular substantially shorter than the height of the forming bell to reduce the maximum the volume of said forward part of the sterile enclosure 16.

The slide 14 in which the cover strip 12 is guided passes above the heating drum 15 the heating cylinder 17, the forming station 18 and the filling station 33 and comes to connect with the forward end of the wall 40 (FIG. 1). A transversal wall 41 connects in seal-tight manner the bottom wall 42 of the slide 14 with the wall of the forming bell 20 and extends between the heating station 15, 17 and the forming station 18.

Between the entrance to the sterile enclosure and its connection with the wall 41, the rear part 42a of the bottom wall 42 of the slide 14 constitutes a portion of upper wall of the sterile enclosure 16. Between its connection with the wall 41 and its connection with the wall 40, the forward portion 42b of the bottom wall 42 of the slide overhangs the forming and filling stations and delimits, with the walls 40 and 41, a wall closed on itself which circles the elements of the forming and filling stations situated above the forming bell 20 and the nozzle support 35, outside the sterile enclosure 16.

The forward end of the slide 14 comes flush with the transport plane P of the container strip, the bottom wall of the slide closing the sterile enclosure 16 with its forward end 42c.

Laterally, the enclosure 16 is closed by first flat side walls 43 parallel with one another and which are connected in seal-tight manner, for example by welding, to the rear portion 42a of the bottom wall 42 of the slide 14 and the wall 41, and whose bottom edge conforms to the path of the container strip 11 from the entrance to the sterile enclosure to the entrance under the forming bell. At the forming station, the sterile enclosure is closed laterally by the side walls 20a (FIG. 3) of the forming bell, the wall 11 remaining in contact with the bottom edge of these walls 20a. Downstream of the forming station, the sterile enclosure is closed by flat side walls 44 one parallel with the other, which are connected in seal-tight manner, for example by welding, to the wall 40 and which extend downwards as far as the plane P of transport of the container strip.

To sum up, the sterile enclosure is therefore delimited at the bottom, from its inlet to its outlet, by the sterile side of the container strip 11, with the exception of the part which is in contact with the cylinder 17, the free area of the peripheral surface of the cylinder 17 forming a part of bottom wall of the enclosure 16; said peripheral surface being constantly heated, it is sterile. Above, the sterile enclosure is delimited, from its entrance to its discharge end, by the walls 42a, 41, 40 and 42c, and laterally, by walls 43, 20a and 44.

A fixed horizontal plate 45 extends immediately under the transport plane P from the place where the strip 11 leaves the cylinder 17 as far as the level of the forming bell 20. Another plate 46 extends under the transport plate P downstream of the forming station, substantially from the level of the exit from the forming bell as far as that of the exit from the sterile enclosure 16. The plate 46 is mobile vertically between a position referred to as high (FIG. 2), in which it connects with the bottom edges of the front wall 20b of the forming bell 20, of the side walls 44 and of the wall 42c, and a position referred to as low (FIG. 1), in which it frees the path of the formed and filled containers 22.

The strip 11 follows the bottom edges of the side walls of the enclosure 16 amd its width is greater than the distance between said bottom edges in such a manner that the edges or marginal areas of the strip 11 protrude laterally from each side of the enclosure 16. The conveying of the strip 11 is effected by means of clamps 50 (represented only in FIG. 3) which grip the edges of the strip 11 outside the enclosure 16. The clamps 50 are borne by the links 51 of endless chains 52 passing over drive and return wheels (not represented) and whose path is represented diagrammatically in dot-dash lines in FIG. 1. The clamps 50, links 51 and chains 52 are known per se for the transport of a container strip (see in particular U.S. Pat. No. 3,653,175). The clamps 50 are closed on the edges of the joint strip 10 when they reach the path of said joint strip 10 upstream of the entrance to the sterile enclosure.

At the level of the entrance to the sterile enclosure the clamps 50 are open to permit the separation of the cover strip 12 which enters the slide 14, and they are closed again on the edges of the strip 11 outside the side walls 43.

Figure 6:
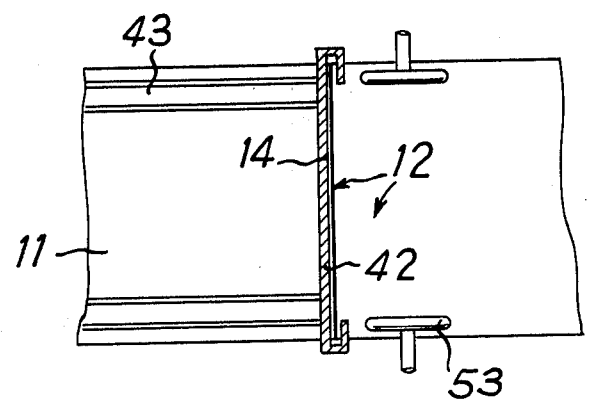
FIG. 6 is a partial cross-sectional view along line VI—VI in FIG. 2.

At the level of the exist from the sterile enclosure the clamps 50 open out again to permit the superimposition of the strips 11 and 12 along their edges and their seal-tight application along these edges by a pair of pressing rollers 53. The clamps 50 are then closed again onto these superimposed edges as soon as they have been applied one against the other by the rollers 53 (FIG. 6).

It will be noted as an alternative that this application in seal-tight manner of the edges of the strips 11 and 12 may possibly be ensured by the mere closure of the clamps 50 on these superimposed edges.

The opening and the closing of the clamps 50 is controlled, as is known per se, by fixed cam paths situated along the path of the clamps and acting on levers borne by said clamps.

The travel of the cover strip 12 in the slide 14 is controlled by that of the container strip with which said cover strip is solid before entry into the slide 14 and after coming out of said slide.

Figure 4:
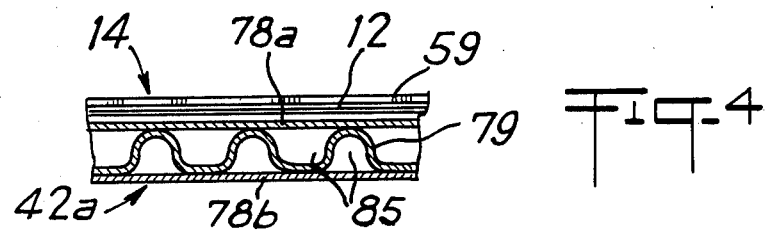
FIG. 4 is a view in longitudinal section and on an enlarged scale of part of the guiding slide of the cover strip in the installation represented in FIG. 1.
Figure 5:
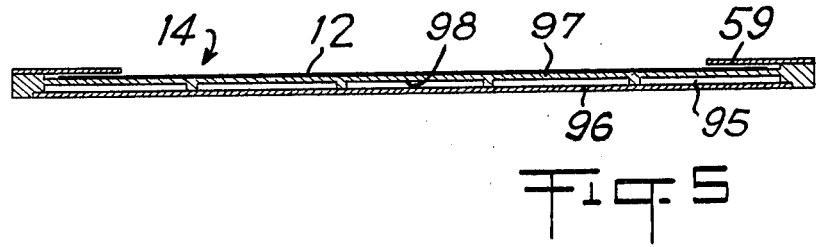
FIG. 5 is a view in cross-section of an alternative embodiment of a guiding slide for the cover strip.

The slide 14 thus constitutes a guide for the cover strip 12. As illustrated in FIGS. 4 and 5, the slide has side edges 59 which are folded back over the marginal areas of the non-sterile side 12a of the cover strip 12. The walls of the slide 14 face therefore the entire sterile side of the strip 12 and the marginal areas of the non-sterile side.

The line along which the strips 11 and 12 are again joined constitutes the exit from the sterile enclosure 16. Then, the cover strip 12 is sealed on the container strip, around the filling opening of the latter, to a sealing station 54 comprising, as known per se a heating electrode 55 and a counter-electrode 56 which are mobile vertically respectively above and below the transport plane P. The sealed containers are then despatched towards a cutting station and, if need be, an over-packing station (not represented). Possibly, a cover strip 57 taken from a storage roll (not represented) and passing over return and guiding rollers 58 is brought over the cover strip 12, between the covering station—constituted by the rollers 53—and the sealing station. The strip 57 is sealed on the strip 11 over the cover strip 12 and around the filling opening of the containers 22.

The inside of the enclosure 16 as well as the inside of the slide 14 on the side of the sterile face of the cover strip 12 are supplied with sterile gas, for example with sterile air at a pressure slightly in excess of that prevailing outside, in a non-sterile atmosphere. This slight excess pressure aims simply at preventing a contamination by infiltration along the edges of the container and cover strips. Sterile air thus escapes permanently along the bottom edges of the sterile enclosure an along the edges 9 of the slide.

The device 60 for supplying pressurized sterile air is housed in the transverse tunnel which contains the upper elements of the forming and filling stations, between said stations. The air supplied by a duct 61 passes through an absolute filter 62 and reaches a first cavity 63 of a body 64. Ducts 65 establish a communication between the cavity 63 and a first chamber 66 of which a wall is constituted by a flexible membrane 67 which isolates in seal-tight manner the chamber 66 from a second chamber 68 into which a duct 69, connected with a source of pressurized fluid, opens out. Ducts 70 connect the chamber 66 with a second cavity 71 of the body 64. The admission of pressurized fluid into the chamber 68 produces the deformation of the membrane 67 which seals the openings of the ducts 65 and 70 opening out into the chamber 66 and thus isolates cavity 63 from cavity 71.

The sterile air is introduced into the enclosure 16 through an opening 72 in the wall 40 by means of a tubular duct 73 which connects in sealtight manner the cavity 71 with the opening 72.

The bottom wall of the slide 14 has for example openings (not represented) which communicate with internal passages provided in said bottom wall and connected with the cavity 71 by means of a duct (not represented) in such a manner as to supply the bottom of the slide with sterile air at a pressure slightly in excess of that prevailing on the side of the non-sterile face of the cover strip. This sterile air can thus constitute an air strip or air cushion under the cover strip permitting a floating guiding of said strip. The air escapes along the edges of the strip. A protection cover, preferably perforated to permit the escape of the sterile air may be placed on the slide. It will be noted as an alternative that the guiding of the cover strip may be made in a duct in the shape of a tunnel or chute with a bottom wall having grooves connected to the cavity 71 and with an upper wall provided with escape passages.

To prevent any risk of contamination of the sterile enclosure by germs introduced by the rod 25 bearing the forming punches, at the time of its vertical alternating motion through the sleeve 26, a sterile atmosphere is made to prevail in an annular area which surrounds said rod in its portion situated above the forming bell. A tube 75 inside which the rod 25 passes is fixed to the sleeve 26. The tube 75 is closed at its bottom end, open at its top end, and is connected to the cavity 71 by a duct 76. A tube 77, having a diameter greater than that of tube 75, is solid with the rod 25. The tube 77 is closed at the top, open at the bottom end, and surrounds the top part of the rod 25. Tubes 75 and 77 are designed in such a manner that at least the bottom end portion of the tube 77 surrounds the top end portion of the tube 75 when the rod 25 is in high position (FIG. 2). Thus, a sterile atmosphere with a pressure slightly in excess of outside pressure, is permanently held around the portion of the rod 25 which protrudes above the forming bell.

All the walls along which the cover strip 12 and the container strip 11 pass between the entrance to, and the exit from the sterile enclosure, i.e. the drum 15 and the cylinder 17, the entirety of the bottom wall 42 of the slide 14 and the walls 46 are provided with incorporated heating means. Similarly, all the rigid walls which delimit the enclosure 16, that is to say, in the example illustrated, the rear portion 42a of the wall 42, the side walls 43, the wall 41, the wall 40, the side walls 44 and the end front portion 42c of the wall 42 are also provided with incorporated heating means.

Preferably, these heating means consist in the presence of one or more internal passages for the circulation of a hot fluid.

FIGS. 7 to 11 illustrate various methods of embodiment of an enclosure wall provided with inner passages and able to be used for the installation in accordance with the invention.

The enclosure wall represented in FIGS. 7 and 9 has a first metal plate 80, in a good heat-conductive material, for example stainless steel a free face of which 81 is intended to constitute subsequently the inner face when building an enclosure.

Against the other side 82 of the plate 80 a corrugated plate 83 is applied. Plate 83 is in contact with the face 82 along crest lines of its corrugations and delimits with said face 82 ducts 85 between said crests.

The ducts 85 are parallel one with the other, connected in parallel at one end with a fluid supply duct 86 and at the other end with a fluid outflow duct 87. The ducts 85, with the ducts 86 and 87 constitute an internal circulation circuit for a fluid, and inlet 86a and outflow 87a connections may be provided on the ducts 86 and 87 to connect this internal circuit to an external circuit.

The fixing of the plates 80 and 83 may be made by welding along their edges and may be completed by bolts 88 screwed on threaded rods 89 welded on the external face 82 of the plate 80.

Insulation between adjoining ducts 85 may be completed by the interposition of seals, for example rubber strips (not represented) placed between the plate 80 and the corrugation crests 84.

FIG. 11 illustrates an alternative embodiment of the wall represented in FIGS. 7 and 9. According to said alternative, the ducts 85 are constituted by corrugations 90 of the plate 83, corrugations separated one from the other by flat sections 91 applied against the face 82 of the plate 80.

FIGS. 8 and 10 further illustrate another method of embodiment of a wall according to the invention. It still comprises a first metal plate 80 with its smooth inner face 81. On the other face 82 of the plate 80 tubular elements 93 are fixed: they are parallel one with the other and constituted by curved or folded back strips, folded throughout their length with their longitudinal edges 93a, 93b which are rectilinear and welded on the face 82. The tubular elements 93 also have the shape of not completely closed tubes constituting, with face 82, ducts 85 for the flow of a liquid.

Ducts 85 are parallel one with the other. They may be connected in parallel between two supply and removal ducts, as described hereinabove with reference to FIG. 7. These ducts may also be connected between them in series, by means of duct sections 94 (FIG. 8) connecting their ends to constitute an internal series circuit for the flow of a liquid.

In the case of the bottom wall of the slide 14, the ducts 85 are formed (FIG. 4) by the corrugations of a corrugated plate 79. The plate 79 is applied against a face of a flat plate 78a whose other face, preferably smooth, forms the bottom of the slide 14. In FIG. 4 a representation has been given of a section of the rear portion 42a of the slide 14. The corrugated plate 79 is in this case covered on each side by a flat plate, 78a, 78b, as this part of wall 42a delimits on one side the slide 14 and on the other side forms a portion of top wall of the enclosure 16.

Naturally, further methods of embodiment of walls with incorporated fluid circuit may be adopted. Thus, for example, for the slide 14 (FIG. 5) passages 95 for a fluid are delimited by fixing a flat plate 96 against a plate 97 having on its surface grooves or cells 98.

All the internal passages formed in the walls 40, 41, 42, 43, 44, 45 and 46 are connected to a heating fluid supply circuit (not represented).

The walls of all the passages along which the sterile air passes before being released into the enclosure and into the slide may also be provided with heating means incorporated in the form of passages for the circulation of a fluid. Thus, as represented in FIG. 2, the body 64, tube 73 and duct 76 are surrounded by a double wall whose inner volume is connected to the heating fluid supply circuit. Similarly, finally, passages 99 are provided in the wall of the forming bell, at least in the vicinity of its bottom edge and possibly in the nozzle support wall, passages 99 themselves also connected to the heating fluid supply circuit.

As described hereinafter, these heating means are provided for sterilising with heat the walls whose internal face delimits the enclosure or to sterilize at the same time each wall a face of which is situated in the vicinity of a section of container or cover strip, and the face of the strip section facing said wall. Thus, it is important that these walls, at least on the side having the face to be sterilized which delimits the enclosure or faces a strip section, should be made in a good heat conducting material, for example metal, and in particular stainless steel. Moreover, it is also preferable that the faces to be sterilized of these walls should be smooth to prevent any danger of survival of germs in cavities or corners difficult for heat to reach.

The heating fluid supply circuit may constitute, with the various inner passages of the walls of the enclosure, a closed circuit provided with means permitting establishing a forced circulation of the fluid and means for the regulation of the temperature of said fluid.

The heating fluid used may be air or a pressurized fluid, for example dry water steam. Its temperature and the time during which it is made to circulate are selected in such a manner as to keep the inner surface of the walls at a temperature comprised preferably between about 125° C. and 150° C. for a period preferably comprised between 15 and 30 minutes. The first plate of the walls being generally constituted by a metal which is a good conductor of heat, these temperature and time values may apply to the temperature of the hot fluid and the time during which it is circulated.

Before circulating the hot fluid in the inner passages of the walls to be sterilized, it will be possible to proceed with the moistening of the inner faces of these walls to be sterilized.

It has indeed been noted that such a moistening may make it possible to reduce by about one quarter the length of time necessary for full sterilization of the walls of the enclosure by the heat supplied by the heating fluid.

The installation described hereinabove operates as follows (FIG. 2):

On starting, the installation is cleaned out. The sterile air supply ducts such as 73 and 76 are cleaned by circulating a liquid, membrane 67 isolating the cavity 71 of the upstream section from the air supply. Then, the rigid walls 40 to 44 delimiting the enclosure, the slide and the bottom walls 45 and 46 are cleaned, the wall 46 being in low position, then the wall 46 is placed in high position to close the enclosure.

The end of the joint strip is separated into an end cover strip section which is made to pass into the slide as far as the level of the outflow from the enclosure, and into an end container strip section which is made to pass along the path of said strip without commissioning the forming and filling sections, until the exit from the enclosure. The ends of these sections are joined in sealtight manner on coming out from the enclosure 16 which is then substantially closed.

The sterile air is introduced into the enclosure 16 and into the slide 14, while a hot fluid, for example dry water steam at a temperature of about 140° C. is sent into the inner passages of all the walls provided with in-built heating means. The heat supplied by the steam sterilizes the faces of said walls which face the inside of the enclosure and the container and cover strips. Thus, the initially sterile faces of the end sections of the container and cover strips, faces which may be contaminated when said sections have been separated from each other and then joined to form the enclosure, are sterilized by the heat supplied by the walls along which these sections are placed. Hot water continues to be passed for the length of time necessary to effect perfect sterilization.

When sterilization is completed, and if the drum 15 and the return cylinder 17 have been previously heated, the packing operation proper may start. The container and cover strips are moved step by step and synchronously by being gradually separated each from the other at the entrance to the sterile enclosure. The operation of the forming, filling and sealing stations is then launchedm the wall 46 having been brought back to the low position. The containers 22 are then successively formed, filled and sealed according to sequences well known per se.

If need be, after sterilization, a cold fluid, for example water, may be passed in the inner passages of the previously heated walls so as to cool the latter.

During the packing operation, the walls of the sterile enclosure, in particular walls 40 and 44, may be held at a given temperature by circulation of a fluid in their inner passages in such a manner as to prevent the condensation and drip phenomena on said walls.

FIGS. 12 to 15 illustrate other methods of embodiment of the installation in accordance with the invention. The elements common to the installations represented respectively in FIGS. 1 to 6 and FIGS. 12 to 15 bear the same references and will not be again described in detail hereinbelow.

The installation represented diagrammatically in FIGS. 12 and 13 is distinguished from that described hereinabove particularly in that the cover strip 12 after its separation from the container strip 11, constitutes, with its sterile face, the upper wall of the sterile enclosure 16.

Between its entrance formed by the line of separation of the container and cover strips and its delivery formed by the line where these strips meet, the sterile enclosure 16 is therefore delimited at the bottom essentially by the container strip, as in the case of the installation described hereinabove, at the top by the cover strip and laterally by two vertical parallel side walls 101 whose top and bottom edges follow respectively the path of the cover strip and that of the container strip.

The cover strip 12 passes therefore against the upper edges of the side walls 101 and its width is greater than the distance between said edges. The border areas of the cover strip 12 protrude therefore laterally from each side of the enclosure and are gripped, outside the enclosure, by clamps 102 similar to clamps 50. The clamps 102 are borne by the links 103 of endless chains whose path 104 is represented diagrammatically in mixed dash-dot lines in FIG. 12. These clamps, in cooperation with the upper edges of the walls 101 guide the cover strip along its own path from its separation from the container strip, over the forming and filling stations, and until it joins the container strip, a joining effected by the pressing rollers 53.

As in the installation represented in FIG. 1, the upper elements of the forming 18 and filling 33 stations, as well as the device 60 for supplying sterile air, are housed outside the sterile enclosure in a transverse tunnel.

This tunnel 105 is delimited by a horizontal bottom wall 106 which is connected to the side walls 101 and overhangs the transport plane P. On this wall 106 the forming bell and the nozzle support are mounted, and this wall comprises the opening 72 connected to the device for supplying sterile air. This wall 106 is preferably situated at a distance from plane P shorter than the height of the forming bell. A wall in the shape of an upturned U 107, passing above the forming and filling stations and aove the device for supplying sterile air, is connected to the ends of wall 106.

Openings 108 are formed in the side walls 101, along the sides of the walls 106 and 107, openings which establish the communication of the tunnel 105 with the outside.

A cover wall 109 extends above the cover strip 12 substantially from the entrance of the sterile enclosure 16 as far as the delivery of said enclosure. This covering wall 109 has a section in the shape of an upturned U, with wings situated substantially along the extension of the side walls 101. The cover strip 12 is thus in some way guided with its edge areas passing in slits 110 (FIG. 13).

According to the method of embodiment represented in FIG. 14, the joint strip 10 passes on one side of the vertical ramp 120 of radiation heating elements and then the cover strip 12 is separated from the container strip 11 and guided along its own path while the heating of the container strip 11 is continued by making it pass on the other side of the ramp 120 and then over a return heating cylinder 121 which brings the strip 11 into the plane P.

The start of a packing operation and its unfolding in an installation such as that represented in FIG. 12 or FIG. 14 are such as described hereinabove for the installation represented in FIG. 1.

In particular, the cover wall 109—which in the case of the installation represented in FIG. 14 may be extended towards the rear along the path of the joint strip facing the ramp 120—in the same way as the walls 45 and 46 is provided with incorporated heating means constituted by one or more internal passages for the circulation of a heating fluid. Similarly, the side walls 101 and the transversal walls 106 and 107 are provided with built-in heating means of the same type. Moreover, the enclosure 16 is supplied with sterile air by the device 60, as described hereinabove, in such a manner as to maintain inside the enclosure an excess pressure which is just adequate to prevent the outside air from entering it along the edges of strips 11 and 12.

Finally, FIG. 15 illustrates another method of embodiment of the installation according to the invention. The container strip 11 is separated from the cover strip 12 at the entrance to the slide 14, at the level of the junction between the bottom wall of the slide 14 and a wall 130 which connects said bottom wall to the entrance of the forming station.

Wall 130 is a guide wall for the container strip up to the forming station. This guide wall can constitute the bottom wall of a slide with a structure similar to that of slide 14.

The container strip is guided along wall 130 with its face intended to form subsequently the inside of the containers facing wall 130. The latter is provided with built-in heating means, in particular internal passages for the circulation of a heating fluid, to be able to be sterilized.

The heating of strip 11 so that it reaches forming temperature is effected by a heating plate 131 in front of which strip 11 passes as it travels along wall 130. The heating plate 131 is external to the sterile enclosure and heats strip 11 by radiation. Plate 131 carries in-built heating means, for example electric resistors or a hot fluid heating circuit.

In the foregoing, mention has been made of the use of clamps borne by endless chains for the transport of the container strip as well as, directly or indirectly for the transport of the cover strip, As an alternative, at least one of these strips may be conveyed by means of conveyor bands bearing studs embedded in the edges of said strip, preferably on the non-sterile side. The edges of the strips solid with the bands are then guided in lateral slides solid with the side walls of the enclosure, at the level of the path of the strip. Such transport by means of bands is described in French Patent Application No. 75/38785.

Finally, it will be noted that the use of a joint strip comprising the container strip and the cover strip with each having a sterile face, the use of walls provided with in-built heating means, along the paths of the strips and as enclosure wall, with a preferably smooth inner face, and the housing outside the enclosure of the elements of the forming and filling stations situated above the forming bell and the nozzle support, as well as all the elements of transport of the strips, contribute to facilitate considerably the making of a sterile enclosure and its being kept in a sterile condition, and permit a fast and easy starting of the installation. It may also particularly be noticed that the heating of the container strip to forming temperature by passing over one or more drums at controlled temperature permits an immediate restart in the event of a temporary stop in operation, as the container strip will have been held, without overheating, at its forming temperature during the stop.

Naturally, various alterations or additions may be made to the methods of embodiment of the process and installation according to the invention described hereinabove, without on that account departing from the scope of protection defined by the attached claims. In particular, it is possible to envisage the use of a treble joint strip with an intermediate strip which has two sterile faces and is placed between the sterile sides facing the container and cover strips, the three strips being applied one on the other in seal-tight manner at least along their sides. The intermediate strip must be detached from the container strip upstream of the entrance into the forming station and must be detached from the cover strip upstream of the place where the latter is applied on the container strip on leaving the enclosure. After its separation from the other two strips, the intermediate strip is removed to the outside of the sterile enclosure or of the guiding slide, passing through a slit of a wall of the enclosure or of the bottom of the slide.

I claim:

1. In a process for packing a product in a sterile medium wherein containers are formed in a strip of thermoplastic material by hot forming of the thermoplastic material in a forming station, the container strip being sterile at least on the side forming the inside of the containers, the formed containers being filled in a filling station, the forming and filling of the containers being made in a sterile enclosure in which a slight excess pressure prevails as compared with the non-sterile external atmosphere, and which enclosure comprises side walls and an upper wall, as well as a bottom wall constituted, at least in part, by the container strip, the filled containers being covered with a strip without their inside being able to become contaminated by the non-sterile atmosphere, at least the face of said strip facing the inside of the containers being sterile, and the cover strip being sealed on the container strip around the filling opening of each container; characterized by using a composite strip constituted by at least the container strip and the cover strip having each a sterile side isolated from outside by application on another sterile side, in seal-tight manner, at least along its sides, the sterile sides of the container strips and cover strips being made to face each other, the container strip and the cover strip are separated at the entrance to the sterile enclosure, causing the cover strip to travel along a path overhanging that of the container strip, as it passes above forming and filling stations, providing a sterile atmosphere with slight excess pressure relatively to the non-sterile outside atmosphere on the side of the sterile face, turned downwards, of the cover strip, moving the container and cover strips along walls provided with incorporated heating means by causing them to pass respectively below and above a non-sterile area containing elements of forming and filling stations, and, outside the sterile enclosure, joining the cover strip and the container strip carrying the filled containers in seal-tight manner at least along their edges.

2. A process according to claim 1, characterised in that, after its separation from the joint strip, the container strip is heated to forming temperature on its path situated between the entrance to the sterile enclosure and the entrance to the forming station.

3. A process according to any one of claim 1, characterised in that the container strip is heated to forming temperature on its path where it forms at least a part of wall of the sterile enclosure.

4. A process according to claim 1, characterised in that the container strip is heated to forming temperature by passing over at least one heating cylinder between the entrance to the sterile enclosure and the entrance to the forming station.

5. A process according to claim 1, characterised in that, among the cover strip and the container strip, at least the container strip is moved along the sterile enclosure, by making its edges protrude laterally from each side of the enclosure, and said strip being conveyed by gripping its edges from outside the enclosure.

6. A process according to claim 1, characterised in that, among the cover strip and the container strip, at least one strip is moved, by guiding it, at least along its edges, in guiding slides.

7. A process according to claim 6, characterised in that the strip is conveyed, whose edges are guided along guiding slides with the aid of conveyor bands which are made solid with at least places with a space between them, of the longitudinal edges of said strip on the side of its non-sterile face.

8. A process according to any claim 1, characterised in that the cover strip is made to pass, on its own path, between the entrance to, and the exit from the sterile enclosure, in a passage in the form of a slide or chute whose bottom wall faces the sterile side of the cover strip and is provided within corporated heating means and whose side walls cover the strip at least along its marginal areas, in the space between the bottom of the channel and the sterile side of the cover strip, a sterile atmosphere with a slight excess pressure in relation to the non-sterile external atmosphere.

9. A process according to claim 1, characterised in that the cover strip is used to form at least partly the upper wall of the sterile enclosure and the cover strip and the container strip, between the entrance to, and the exit from the sterile enclosure, are made to pass respectively above and below a non-sterile transverse tunnel which goes through the sterile enclosure, is isolated from it in seal-tight manner, opens outside and contains upper elements of the forming and filling stations.

10. A process according to claim 1, characterised in that at the exit from the sterile enclosure the junction is made of the edges of the cover strip with those of the container strip by means of pairs of pressing rollers.

11. A process according to claim 1, characterised in that, at the exit from the sterile enclosure, the edges of the cover strip and those of the container strip are joined together by means of clamps which constitute the conveying means of the container strip by gripping its edges outside the sterile enclosure.

12. A process according to claim 1, characterised in that, after the application of the cover strip onto the container strip at the exit from the sterile enclosure, a covering strip is applied on the cover strip and said covering strip is sealed on the containers.

13. A process according to claim 1, characterised in that, in order to start the packing operation, the end section of the joint strip is separated into a container strip section and a cover strip section, the enclosure which is to be sterile being closed by means of the cover strip section and the container strip section, causing these sections to pass along rigid walls provided with built-in heating means, and the free-ends of these sections being joined in seal-tight manner at the exit from the sterile enclosure, the inner faces of all the walls of the enclosure being sterilised by means of the said built-in heating means, while supplying the inside of the enclosure with sterile gas at a pressure slightly in excess of the pressure of the external non-sterile medium, and, when the sterile enclosure has been formed, the forming and filling only of the containers is proceeded with, by moving step by step and synchronously the container strip and the cover strip, while separating them from each other at the entrance to the sterile enclosure.

14. A process according to claim 13, characterised in that, in order to form at the start the sterile enclosure, a hot fluid is caused to circulate in internal passages provided in rigid walls whose inner faces delimit the sterile enclosure or extend along the said sections of container strip and cover strip, between the entrance to, and the exit from the enclosure.

15. A process according to claim 14, characterised in that the said hot fluid is made to circulate after the moistening of the said inner faces of the walls.

16. A process according to claim 1, characterised in that, after sterilization of the enclosure, the said internal faces of the said rigid walls are held substantially at a predetermined temperature by means of the circulation of fluid in the internal passages of the said walls, in a manner to prevent condensation against the said internal faces during the packing operation.

* * * * *